United States Patent [19]

Staendeke

[11] 4,096,189

[45] Jun. 20, 1978

[54] PRODUCTION OF TERTIARY PHOSPHINE OXIDES

[75] Inventor: Horst Staendeke, Bruhl, Germany

[73] Assignee: Hoechst Aktiengesellschaft, Frankfurt am Main, Germany

[21] Appl. No.: 696,921

[22] Filed: Jun. 17, 1976

[30] Foreign Application Priority Data

Jun. 21, 1975 Germany ............................. 2527796

[51] Int. Cl.² ............................................... C07F 9/53
[52] U.S. Cl. .............................................. 260/606.5 P
[58] Field of Search ................................. 260/606.5 P

[56] References Cited

U.S. PATENT DOCUMENTS

| 3,325,546 | 6/1967 | Hays ..................... 260/606.5 P |
| 3,520,939 | 7/1970 | Brennan ................ 260/606.5 P |
| 3,751,482 | 8/1973 | Weinberg ............... 260/606.5 P |
| 3,784,638 | 1/1974 | Lambert ................ 260/606.5 P |

OTHER PUBLICATIONS

Chemical Abstracts 66, 38015j (1967).
Kosolapoff, Organic Phosphorus Compounds, Wiley--Interscience, N.Y. V1 pp. 47 to 49 (1972).
Kosolapoff Organic Phosphorus Compounds, Wiley--Interscience, N.Y. V2 pp. 207-208 (1972).
Kosolapoff Organic Phosphorus Compounds, Wiley--Interscience N.Y. V3 pp. 343-346.

*Primary Examiner*—Helen M. S. Sneed
*Attorney, Agent, or Firm*—Connolly and Hutz

[57] ABSTRACT

Production of tertiary phosphine oxides of the general formula $$R^1R^2R^3P(O),$$

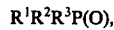

in which $R^1$, $R^2$ and $R^3$ each stand for identical or different, substituted or unsubstituted alkyl, aryl or aralkyl groups. The tertiary phosphine oxides are produced by oxidizing at temperatures higher than 200° C one or more quaternary phosphonium halides of the general formula $$[R^1R^2R^3R^4P]\,X,$$

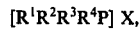

in which $R^1$ through $R^3$ have the meanings given above, $R^4$ has the same meaning as $R^1$ through $R^3$, and X stands for a halogen atom.

5 Claims, No Drawings

PRODUCTION OF TERTIARY PHOSPHINE OXIDES

The present invention relates to a novel process for making tertiary phosphine oxides of the general formula:

$$R^1R^2R^3P(O)$$

in which $R^1$, $R^2$ and $R^3$ each stand for identical or different, substituted or unsubstituted alkyl, aryl or aralkyl groups.

It has been described that tertiary phosphine oxides can be obtained, for example, by oxidizing tertiary phosphines, by subjecting quaternary phosphonium hydroxides to thermal decomposition or by subjecting quaternary phosphonium halides to alkaline hydrolysis (G. M. Kosolapoff/L. Maier, Organic Phosphorus Compounds, vol. 3, Wiley-Interscience, New York (1972)). Further known processes comprise reacting phosphorus halides with organo-metal compounds, e.g. in accordance with the following reaction equation:

$$P(O)X_3 + 3\ R\ MgX \rightarrow R_3P(O) + 3\ MgX_2$$

or the additive combination of olefins, aldehydes or ketones with primary or secondary phosphine oxides, e.g. in accordance with the following equation:

$$R_2^1 P(O)H + R_2CH = CH_2 \rightarrow R_2^1 P(O)R^3$$

These processes are, however, not fully satisfactory in respect of the following points: they can scarcely be effected on a commercial scale or use starting materials which have to be made by a plurality of steps and which are accordingly expensive.

The present invention now unexpectedly provides a process for making tertiary phosphine oxides, which comprises oxidizing at temperatures higher than 200° C one or more quaternary phosphonium halides of the general formula:

$$[R^1R^2R^3R^4P]\ X$$

in which $R^1$ through $R^3$ have the meanings given above and $R^4$ has the same meaning as $R^1$ through $R^3$, and X stands for a halogen atom.

Preferred features of the present process provide:
for air, oxygen, steam or a mixture thereof to be used as an oxidizing agent;
for the oxidation to be effected at temperatures of 300° up to 450° C;
for the chlorides or bromides to be used as the quaternary phosphonium halides;
for the resulting vaporous oxidation product to be condensed or absorbed in a liquid; and
for concentrated hydrochloric acid to be used as the absorbing liquid.

Tetramethylphosphonium chloride has been found to behave thermally different in a stream of inert gas or air (cf. Table 1 below). As can be seen, the present process provides for the quaternary phosphonium chloride to be oxidized at temperatures lower than the pyrolyzing temperature. In other words, it does not provide for the compound to be first pyrolyzed and for the resulting tertiary phosphine to be then oxidized in contact with air.

Table 1

| Temp. °C | Thermogravimetric analysis of tetramethylphosphonium chloride. | |
|---|---|---|
| | Loss in weight in mg/h | |
| | $N_2$-stream (10 l/h) | Air-stream (10 l/h) |
| 330 | <0.5 | 5 |
| 350 | <0.5 | 20 |
| 380 | 1 | 79 |
| 400 | 12 | 86 |
| 420 | 51 | 128 |

The present process, which is the first to permit, e.g. the production of low tertiary phosphines from hydrogen phosphide and tetralkylammonium halides made in the manner described in German patent appln. No. P 24 57 442.3, compares very favorably in this respect with the prior art methods.

Tertiary phosphine oxides find widespread uses as detergents, dyeing aids, catalysts, corrosion inhibitors and also as interesting intermediates in the production of flameproofing agents, plant protecting agents and pharmaceutical preparations.

EXAMPLE 1

24.3 g of tetramethylphosphonium chloride [$(CH_3)_4P$]Cl was heated to 420° C in a stream of nitrogen/steam (about 10 l $N_2$/h and about 20 g $H_2O$/h). The resulting phosphorus-containing reaction products were condensed in a cooled trap or absorbed in a gas scrubbing bottle (filled with hydrochloric acid). The resulting solutions were subjected to NMR-spectroscopy and found to contain 7.2 g of trimethylphosphine $(CH_3)_3P(O)$, corresponding to a yield of 41% of the theroretical.

EXAMPLE 2

22.6 g of tetramethylphosphonium chloride [$(CH_3)_4P$]Cl was heated to 420° C in a stream of air/steam (about 10 l/h air and about 20 g/h $H_2O$). The resulting phosphorous-containing reaction products were condensed in a cooling trap or absorbed in a gas scrubbing bottle (filled with concentrated hydrochloric acid). The resulting solutions were subjected to NMR-spectroscopy and found to contain 12.0 g of trimethylphosphine oxide $(CH_3)_3P(O)$, corresponding to a yield of 73% of the theoretical.

EXAMPLE 3

22.8 g of tetramethylphosphonium chloride [$(CH_3)_4P$]Cl was heated to 380° C in a stream of air (about 15 l/h air). The resulting phosphorus-containing reaction products were condensed in a cooling trap or absorbed in a gas scrubbing bottle (filled with concentrated hydrochloric acid).

The resulting solutions were subjected to NMR-spectroscopy and found to contain 13.8 g of trimethylphosphine oxide $(CH_3)_3P(O)$, corresponding to a yield of 83% of the theoretical.

I claim:
1. A process for making tertiary phosphine oxides of the general formula

$$R^1R^2R^3P(O)$$

in which $R^1$, $R^2$ and $R^3$ each stand for identical or different, alkyl, aryl or aralkyl groups, which comprises oxidizing at temperatures higher than 200° C quaternary phosphonium halides of the general formula $[R^1R^2R^3R^4P]\,X$ in which $R^1$ through $R^3$ have the meanings given above, $R^4$ has the same meaning as $R^1$ through $R^3$, and X stands for a halogon atom, and condensing or absorbing in a liquid the vaporous reaction products thus obtained.

2. The process as claimed in claim 1, wherein air, oxygen, steam or a mixture thereof is used as an oxidizing agent.

3. The process as claimed in claim 1, wherein the oxidation is effected at temperatures of 300 up to 450° C.

4. The process as claimed in claim 1, wherein the quaternary phosphonium halides are the chlorides or bromides.

5. The process as claimed in claim 1, wherein the absorbing liquid is concentrated hydrochloric acid.

* * * * *